(12) United States Patent
Vaidya et al.

(10) Patent No.: US 12,374,438 B1
(45) Date of Patent: Jul. 29, 2025

(54) APPARATUS AND METHODS FOR PREDICTION OF REPEAT ABLATION EFFICACY

(71) Applicant: Anumana, Inc., Cambridge, MA (US)

(72) Inventors: Suthirth Vaidya, Bengaluru (IN); Rakesh Barve, Bengaluru (IN); Animesh Agarwal, San Mateo (CA); Samir Awasthi, Boston, MA (US); Murali Aravamudan, Andover, MA (US); Maulik Nanavaty, Cambridge, MA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/809,611

(22) Filed: Aug. 20, 2024

(51) Int. Cl.
G16H 20/40 (2018.01)
A61B 5/00 (2006.01)
A61B 5/346 (2021.01)
A61B 5/364 (2021.01)
A61B 18/00 (2006.01)
(Continued)

(52) U.S. Cl.
CPC ............ G16H 20/40 (2018.01); A61B 5/346 (2021.01); A61B 5/364 (2021.01); A61B 5/7246 (2013.01); A61B 5/742 (2013.01); A61B 18/1492 (2013.01); A61B 34/10 (2016.02); G16H 10/60 (2018.01); G16H 50/70 (2018.01);
(Continued)

(58) Field of Classification Search
CPC ........ G16H 20/40; G16H 10/60; G16H 50/70; A61B 34/10; A61B 5/364; A61B 5/7246; A61B 5/742; A61B 5/346; A61B 2034/104; A61B 18/1492; A61B 2018/00577
See application file for complete search history.

(56) References Cited

U.S. PATENT DOCUMENTS 10,154,888 B2   12/2018   Sagon et al.
11,540,796 B2   1/2023    Madabhushi et al.
(Continued)

OTHER PUBLICATIONS

Tang et al., "Machine Learning-Enabled Multimodal Fusion of Intra-Atrial and Body Surface Signals in Prediction of Atrial Fibrillation Ablation Outcomes," Circ Arrhythm Electrophysiol. 2022;15:e010850. DOI: 10.1161/CIRCEP.122.010850. (Year: 2022).*

(Continued)

Primary Examiner — Jonathon A. Szumny
(74) Attorney, Agent, or Firm — Caldwell Intellectual Property Law

(57) ABSTRACT

An apparatus and method for prediction of pulmonary vein reconnection is disclosed. The apparatus includes an electrocardiogram device, at least a processor, and a memory communicatively connected to the at least a processor, wherein the memory contains instructions configuring the at least a processor to generate ablation evaluation training data, train an ablation evaluation machine-learning model using the ablation evaluation training data, receive, from the electrocardiogram device, the electrocardiogram data, and generate, using the ablation evaluation machine-learning model, ablation evaluation data of the patient, wherein generating the ablation evaluation data of the patient includes inputting, into the ablation evaluation machine-learning model, the electrocardiogram data and receiving as output, from the ablation evaluation machine-learning model, the ablation evaluation data of the patient.

20 Claims, 7 Drawing Sheets

(51) Int. Cl.
*A61B 18/14* (2006.01)
*A61B 34/10* (2016.01)
*G16H 10/60* (2018.01)
*G16H 50/70* (2018.01)

(52) U.S. Cl.
CPC .............. *A61B 2018/00577* (2013.01); *A61B 2034/104* (2016.02)

(56) References Cited

U.S. PATENT DOCUMENTS

| | | |
|---|---|---|
| 11,922,630 B2 | 3/2024 | Trayanova et al. |
| 2020/0060757 A1* | 2/2020 | Ben-Haim .............. A61B 34/10 |
| 2021/0085387 A1* | 3/2021 | Amit .................. A61B 18/1492 |
| 2022/0044787 A1* | 2/2022 | Kaufman ................ G16H 20/40 |
| 2022/0079499 A1* | 3/2022 | Doron ....................... G06N 3/04 |
| 2022/0101530 A1* | 3/2022 | Trayanova .............. G16H 50/20 |
| 2024/0112819 A1 | 4/2024 | Paamand et al. |

OTHER PUBLICATIONS

Wojcik et al., "Repeated Catheter Ablation of Atrial Fibrillation—How to Predict Outcome?—," Circulation Journal vol. 77, Sep. 2013; doi: 10.1253/circj.CJ-13-0308. (Year: 2013).*

Kornej et al., "The APPLE Score—A Novel Score for the Prediction of Rhythm Outcomes after Repeat Catheter Ablation of Atrial Fibrillation," PLoS ONE 12(1): e0169933; doi:10.1371/journal.pone.0169933. (Year: 2017).*

Jan De Pooter et al; Validation of a machine learning algorithm to identify pulmonary vein isolation during ablation procedures for the treatment of atrial fibrillation: results of the PVISION study; Europace. May 2024; 26(5): euae116.

* cited by examiner

APPARATUS AND METHODS FOR PREDICTION OF REPEAT ABLATION EFFICACY

FIELD OF THE INVENTION

The present invention generally relates to the field of medical data analysis. In particular, the present invention is directed to apparatus and methods for prediction of repeat ablation efficacy.

BACKGROUND

Pulmonary vein isolation is a common ablation procedure used to treat atrial fibrillation by electrically isolating the openings of the pulmonary veins from the rest of the heart. Despite initial success, atrial fibrillation recurs in approximately 35% of cases, either due to the heart healing itself and causing vein reconnection, or because the original cause of atrial fibrillation was not addressed. Current methods of confirming vein isolation during the procedure do not effectively predict long-term success. Additionally, current methods of determining whether a repeat ablation procedure is the proper procedure for addressing vein reconnection are lacking.

SUMMARY OF THE DISCLOSURE

In an aspect, an apparatus for prediction of pulmonary vein reconnection is disclosed. The apparatus comprises an electrocardiogram device, wherein the electrocardiogram device is configured to detect electrocardiogram data of a heart of a patient, at least a processor, and a memory communicatively connected to the at least a processor, wherein the memory contains instructions configuring the at least a processor to generate ablation evaluation training data, wherein generating ablation training data comprises retrieving historical electrocardiogram data correlated to historical ablation performance data. The memory further contains instructions configuring the processor to train an ablation evaluation machine-learning model using the ablation evaluation training data. The memory further contains instructions configuring the processor to receive, from the electrocardiogram device, the electrocardiogram data. The memory further contains instructions configuring the processor to generate, using the ablation evaluation machine-learning model, ablation evaluation data of the patient, wherein generating the ablation evaluation data of the patient includes inputting, into the ablation evaluation machine-learning model, the electrocardiogram data and receiving as output, from the ablation evaluation machine-learning model, the ablation evaluation data of the patient.

In another aspect, a method for prediction of pulmonary vein reconnection is disclosed. The method includes detecting, using an electrocardiogram device, electrocardiogram data of a heart of a patient. The method further includes generating, by at least a processor, ablation evaluation training data, wherein generating ablation training data comprises retrieving historical electrocardiogram data correlated to historical ablation performance data. The method further includes training, by the at least a processor, an ablation evaluation machine-learning model using the ablation evaluation training data. The method further includes receiving, by the at least a processor and from the electrocardiogram device, the electrocardiogram data. The method further includes generating, by at least a processor and using the ablation evaluation machine-learning model, ablation evaluation data of the patient, wherein generating the ablation evaluation data of the patient includes inputting, into the ablation evaluation machine-learning model, the electrocardiogram data and receiving as output, from the ablation evaluation machine-learning model, the ablation evaluation data of the patient These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
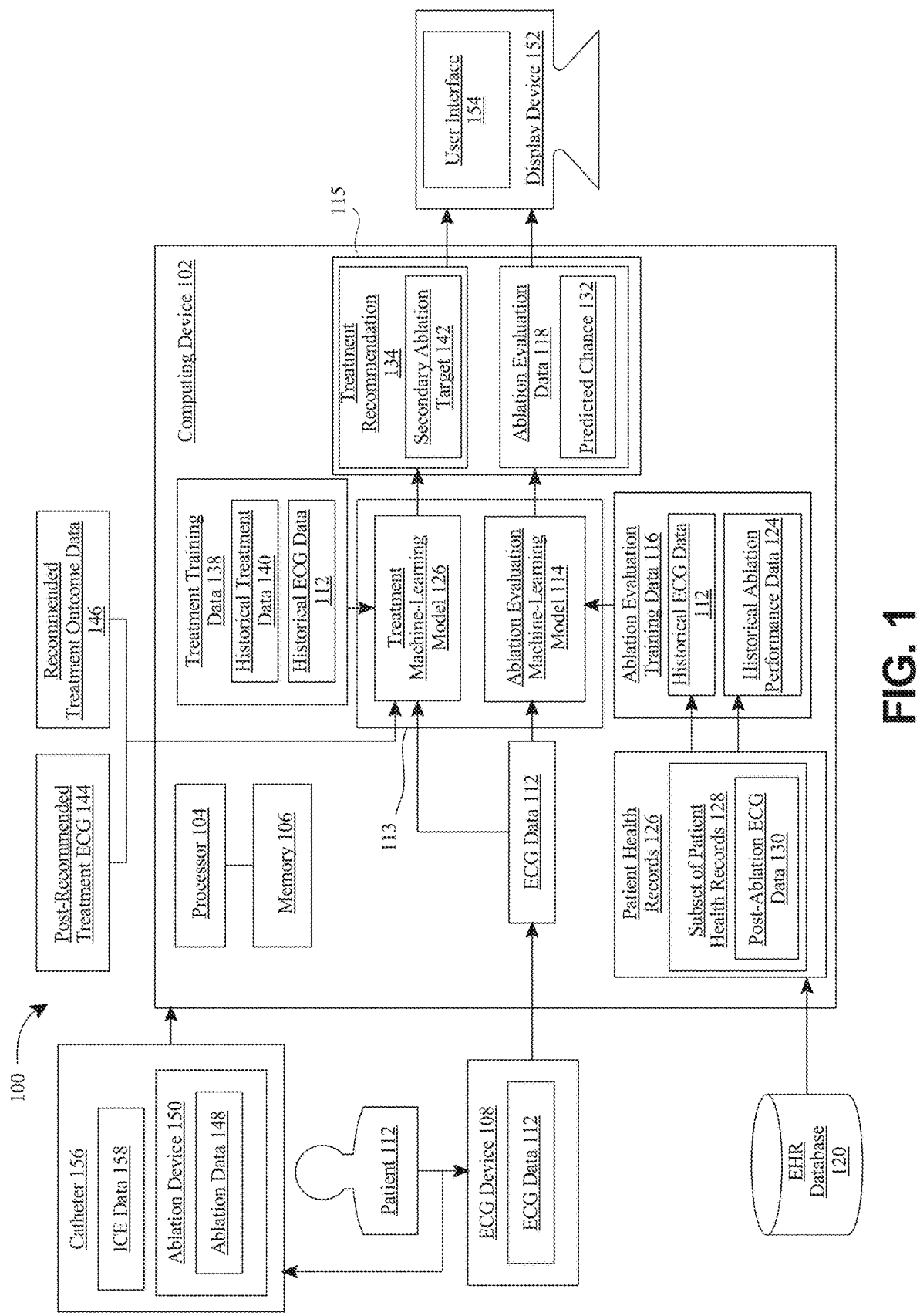
FIG. 1 is a diagram of an exemplary embodiment of an apparatus for prediction of repeat ablation efficacy.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatus and methods for prediction of pulmonary vein reconnection. In an embodiment, the apparatus and methods can implement an apparatus comprising an electrocardiogram device configured to detect electrocardiogram data of a patient's heart, a processor, and a memory containing instructions for the processor. The instructions can configure the processor to generate ablation evaluation training data, train an ablation evaluation machine-learning model using the training data, receive electrocardiogram data from the electrocardiogram device, and generate ablation evaluation data of the patient using the trained model. Aspects of the present disclosure can involve inputting the electrocardiogram data into the ablation evaluation machine-learning model and receiving as output the ablation evaluation data, which may include a predicted chance of pulmonary vein reconnection. In an embodiment, the apparatus may further determine a treatment recommendation using a treatment machine-learning model based on the electrocardiogram data.

Aspects of the present disclosure can be used to predict the likelihood of pulmonary vein reconnection following an ablation procedure. Aspects of the present disclosure can also be used to generate personalized treatment recommendations for patients who have undergone or are candidates for pulmonary vein isolation. This is so, at least in part, because the apparatus utilizes machine learning models trained on historical electrocardiogram data and ablation performance data to analyze a patient's electrocardiogram data and generate ablation evaluation data, including a predicted chance of pulmonary vein reconnection. The apparatus can further employ a treatment machine-learning model to process various inputs, including the electrocardiogram data and ablation evaluation data, to generate tailored treatment recommendations, which may include identifying secondary ablation targets for patients at high risk of reconnection.

Aspects of the present disclosure allow for improved prediction of pulmonary vein reconnection following ablation procedures and generation of personalized treatment recommendations for patients with atrial fibrillation. Aspects of the present disclosure can also be used to identify secondary ablation targets for patients at high risk of reconnection, potentially reducing the need for repeat procedures. Exemplary embodiments illustrating aspects of the present disclosure are described below in the context of several specific examples.

Aspects of the present disclosure address issues associated with post-ablation atrial fibrillation (Afib). A species of post-ablation Afib may include pulmonary vein reconnection. Post-ablation Afib may reoccur in 30% of patients. This causes greater healthcare costs and decreases satisfaction with ablation procedures. In some cases, post-ablation Afib may be corrected by a repeat ablation procedure. For example, post-ablation Afib may be corrected by a repeat ablation procedure in greater than 50% of cases. However, in other cases, post-ablation Afib arises from problems that are not solved by ablation or, in any case, will not be solved by repeat ablation. Aspects of this disclosure address this problem by predicting the efficacy of repeat ablation. This prevents unneeded ablation procedures and increases the success rate for patients. This is an improvement of electrophysiology (EP) systems which have many automatic features and can measure cardiac parameters indicative of current Afib and even measure which electrical paths are the likely cause of Afib, but lack the ability to predict efficacy of repeat treatment.

Referring now to FIG. 1, an exemplary embodiment of an apparatus 100 for prediction of repeat ablation efficacy is illustrated. Apparatus 100 includes a computing device 102. Computing device includes a processor 104 communicatively connected to a memory 106. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, computing device 102 may include any computing device as described in this disclosure, including without limitation a microcontroller, microprocessor, digital signal processor (DSP) and/or system on a chip (SoC) as described in this disclosure, computing device 102 may include, be included in, and/or communicate with a mobile device such as a mobile telephone or smartphone, computing device 102 may include a single computing device operating independently, or may include two or more computing device operating in concert, in parallel, sequentially or the like; two or more computing devices may be included together in a single computing device or in two or more computing devices, computing device 102 may interface or communicate with one or more additional devices as described below in further detail via a network interface device. Network interface device may be utilized for connecting computing device 102 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device, computing device 102 may include but is not limited to, for example, a computing device or cluster of computing devices in a first location and a second computing device or cluster of computing devices in a second location. computing device 102 may include one or more computing devices dedicated to data storage, security, distribution of traffic for load balancing, and the like. computing device 102 may distribute one or more computing tasks as described below across a plurality of computing devices of computing device, which may operate in parallel, in series, redundantly, or in any other manner used for distribution of tasks or memory between computing devices. computing device 102 may be implemented, as a non-limiting example, using a "shared nothing" architecture.

With continued reference to FIG. 1, computing device 102 may be designed and/or configured to perform any method, method step, or sequence of method steps in any embodiment described in this disclosure, in any order and with any degree of repetition. For instance, computing device 102 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 102 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, memory 106 may include a primary memory and a secondary memory. "Primary memory" also known as "random access memory" (RAM) for the purposes of this disclosure is a short-term storage device in which information is processed. In one or more embodiments, during use of the computing device, instructions and/or information may be transmitted to primary memory wherein information may be processed. In one or more embodiments, information may only be populated within primary memory while a particular software is running. In one or more embodiments, information within primary memory is wiped and/or removed after the computing device has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 104 may access the information from primary memory.

With continued reference to FIG. 1, apparatus 100 may include an electrocardiogram device 108. An "electrocardiogram device," for the purposes of this disclosure, is a device that records the electrical activity of a heart over time. In some embodiments, electrocardiogram (ECG) device 108 may be configured to preform electrocardiography.

With continued reference to FIG. 1, electrocardiography is a medical procedure that records the electrical activity of the heart over time, producing an electrocardiogram (ECG or EKG). This process may include placing electrodes on the skin to detect small electrical changes resulting from cardiac muscle depolarization and repolarization during each heartbeat. The ECG may provide a graphical representation of voltage versus time, offering valuable insights into the heart's function and overall cardiac health.

With continued reference to FIG. 1, ECGs may be crucial in identifying various cardiac abnormalities, including rhythm disturbances like atrial fibrillation and ventricular tachycardia, inadequate coronary artery blood flow conditions such as myocardial ischemia and infarction, and electrolyte imbalances like hypokalemia.

With continued reference to FIG. 1, ECG device 108 is configured to detect ECG data 110 of a heart of a patient 112. For the purposes of this disclosure, "ECG data" is data relating to the electrical activity of a heart over time. ECG data may include data from one or more electrodes in contact with the patient's limbs and/or chest. In some embodiments, ECG data may include 12-lead ECG data. For the purposes of this disclosure, "12-lead ECG data," is ECG data that was collected from an electrocardiogram device having 12 leads. A 12-lead ECG may include placing ten electrodes on the patient's limbs and chest surface. This configuration allows the measurement of the heart's electrical potential from twelve different angles or "leads" over a period of typically ten seconds. By capturing the magnitude and direction of the heart's electrical depolarization throughout the cardiac cycle, the ECG may provide a comprehensive view of the heart's electrical activity, enabling healthcare professionals to assess cardiac function and diagnose potential issues.

With continued reference to FIG. 1, in some embodiments, electrocardiogram device 108 may be configured to detect post-ablation arrhythmic electrocardiogram data. For the purposes of this disclosure, "post-ablation arrhythmic electrocardiogram data" is data from an electrocardiogram conducted on a patient that suffers from a cardiac arrhythmia and has undergone an ablation procedure. In some embodiments, post-ablation arrhythmic electrocardiogram data may be representative of a post-ablation arrhythmia of a patient who has previously undergone an ablation procedure.

With continued reference to FIG. 1, a standard embodiment of ECG is a 12-lead ECG, however additional embodiments with fewer leads exist and may be used in this disclosure, such as, without limitation, 6-lead ECGs, like the AliveCor 6-lead ECG, single lead ECGs and the like. ECGs are able to assess cardiac rhythm, detection of myocardial ischemia and infarction, conduction system abnormalities, preexcitation, long QT syndromes, atrial abnormalities, ventricular hypertrophy, pericarditis, and/or other similar conditions. The signals of a patient's heart are shown as waves, which can then be read to indicate potential and current issues with the rhythm of their heart which may implicate certain medical diagnoses. As a nonlimiting example an ECG device 108, may further include, but is not limited to 1-lead, 2-lead, and so on. A 6-lead ECG may include leads I, II, III, aVL, aVF, and aVR. Further information regarding ECG data may be found with reference to FIG. 2.

With continued reference to FIG. 1, in some embodiments ECG data 110 may be extracted from a static image. Static image may be in any image format including without limitation bitmap, joint photographic experts group (jpeg), graphics interchange format (gif), tag image file format (tiff), portable document format (PDF), or the like. Static image may be sourced from a sensor which may include any sensor capable of collecting time series data including, without limitation, a device for capturing an electrocardiogram (ECG), also known as an ECG-enabled device, including without limitation any ECG device having any number of leads and/or electrodes, including without limitation a 12-lead ECG machine such as a Biocare 12-lead ECG machine, a 6-lead ECG machine, an exercise ECG machine, a Holter monitor, a wearable device such as an exercise ECG tracker, a smart watch having a wrist sensor, or the like, and/or any other device capable of capturing ECG data and/or any component thereof. This sensor may alternatively or additionally include any type of device capable of capturing electroencephalograms (EEGs), magnetic resonance imagers, electromyography scans (EMGs), galvanic skin response sensors, fitness trackers, blood pressure monitors, sleep trackers, blood-oxygen level monitors, heart rate trackers, diabetes or herpes trackers, immune disorder logs, or any other medical imaging or time series data capable of being plotted. At least a sensor may refer to standalone devices, such as those used exclusively in established medical facilities, such as magnetic resonance imagers, computerized tomography scans, x-rays, ultrasounds, radiotherapy equipment, intravenous monitors, or any other standalone device. While this disclosure openly discusses medical devices, the disclosure applies to any time series collection devices including non-medical applications wherein the exportable information is limited to static images of the time series data. Additionally, at least a sensor may be a plurality of handheld, or wearable devices such as a Fitbit watch or wristband or other wearable heart rate monitor, a pacemaker or other cardiac rhythm management implant, glucose monitor, smart watch, real-time blood pressure sensors, temperature monitors, respiratory rate monitors or other biosensors, or any other wearable monitor.

Still referring to FIG. 1, for the purposes of this disclosure, "static image time series of measured values" is a digital or printed image compiling information usually derived from a digital device interrogation output, formatted based on the source device protocols and containing time series data capable of being plotted on a two-dimensional axis. As used herein, "static" implies that all image data, metadata, and numerical information contained within the image, even when digitally stored, is inaccessible for processing outside of a human or machine interpreting the image and translating it to a different format that may be interacted with or digitally extracted. In a non-limiting embodiment, a screenshot of a chart is generally considered static data since the data cannot be digitally extracted, but rather only visually observed. Conversely, a dynamic image may include an Excel chart as viewed within Excel, or a time series readout directly within an ECG machine, or any image where the underlying data may be exported to a .csv or similar file format. Static time series image may be in image format, wherein the discrete data points may be identified and interpreted from the image. In other applications of Generative Adversarial Networks, inputs may include a plurality of different types or domains, including without limitation text, code, images, molecules, audio (e.g., music), video, and robot actions (e.g., electromechanical system actions). As a non-limiting example, an ECG recording's data set of voltage measured over a 30-second period at a frequency ranging from 50 Hz-500 Hz may be plotted, recorded, and saved or printed for use by processor 104 as static time series image. Time-plotted voltages, especially within the range of voltages expected to be detected from a human heart through skin contact, exported from any capable device, may be used for static time series image. In a non-limiting embodiment, static time series image may further include any set of plotted time series data which may be valuable within a separate set of domain protocols other than its original static image source.

Still referring to FIG. 1, static time series image, in a non-limiting embodiment may be input in a multitude of source formats including Portable document format (PDF), Portable Network Graphics (PNG), Joint Photographic Experts Group (JPEG), Tagged Image File (TIFF), Bitmap Image File (BMP), Photoshop Document (PSD), Encapsulated Postscript (EPS), Adobe Illustrator Document (AI), Adobe Indesign Document (INDD), Raw Image Format (RAW) or other static image formats. Processor 104 may then convert all static time series image into a single format while converting the data internally, or processor 104 may support direct conversion from each distinct input format option to any designated target domain protocol format.

Still referring to FIG. 1, processor 104 is configured to convert the static time series image into a single format by parsing the received time series of measured values into vector data representing the source data, identifying the specific sensor associated with each vector data when multiple sensors are combined into a single time series, converting the vector data to data points, and scaling and aligning the converted data points. For instance, converted data points may be scaled along a time axis (e.g., horizontal axis) and aligned on a signal axis (e.g., vertical axis). Time axis and signal axis may span two-dimensions; in some cases, time axis may be orthogonal to signal axis. Signal axis may represent signal values, e.g., lead voltage from ECG. As used herein, "parsing" refers to the process of separating and analyzing the individual time series sensor inputs while retaining the relationships between the parsed data and all affiliated data. In a non-limiting embodiment, an ECG may contain twelve or more individual leads, each transmitting a separate time series of voltages plotted over time. Each individual ECG lead time series may be separated into individual vector data sets containing the voltage values and their affiliated times as individual data points, and independently analyzed by processor 104. Processor 104 may additionally enable converting the time series data points to various time-segmented time series data sets. In a non-limiting embodiment, a 10 second ECG time series may be clipped down to a 2.5 second or 5 second ECG, or segmented into these or other smaller time increments as directed by the user.

Further referring to FIG. 1, as a non-limiting example, static time series image may include a patient's blood pressure plotted over a specified time, heart rate, blood-sugar, stress test data, or any relevant time series data associated with a specified initial domain protocol. Static time series image may additionally contain identifying or descriptive data meant primarily to support the targeted time series data. For example, static time series image may include timing information for when the time series was initially recorded, appended notes from medical professionals, location data, or any other appropriate information. These additional data tags embedded within the static time series image may be used as training data to support pairing input data to output data. Specifically, in a non-limiting embodiment, in the example of an ECG time series, various inputs and grouping mechanisms may aid diagnosis of a cardiac irregularity, which may be an indicator of an atrial or ventricular fibrillation. Once confirmed by a medical professional, especially if in multiple instances of repeating similar circumstances, the machine learning model may identify patterns across these instances such that it could grow to act as an early warning system for more severe conditions. Continuing in this non-limiting embodiment, various types of input data included in static time series image may be grouped together in a logical manner to support these types of early warning diagnosis support. In an additional non-limiting embodiment, heart rate training data may support detecting and diagnosing a tachycardia or bradycardia condition, each of which may be indicative of severe or complex issues needing immediate response care. Additionally, blood pressure, electromyography data, computerized tomography (CT) scans, magnetic resonance imaging (MRI), or any other device where data is collected over time and is operative only within an initial domain protocol may be included in static time series image.

Still referring to FIG. 1, static time series image may consist of various ECG formats. In a non-limiting embodiment, a 12-lead ECG may use various recording formats including 3×4, 3×4+R, 3×4+3R, 6×2, 6×2+R, 6×2+3R, 12, 12+R, 12+3R, and/or rhythm mode, then may store the data so recorded within its proprietary system; such a device may enable exporting the collected data to a JPEG, PNG, TIFF, Bitmap, GIF, EPS, RAW image file, or other form of digital image. Additionally, any type of image of time series data may be screenshot and/or printed and subsequently used as input for static time series image. As a further non-limiting example, an ECG machine may use application of Minnesota Code, CSE and/or AHA database formatting guidelines, as well as support for an ECG management system or HL7 protocol. Each of these specified formats and data exchange protocols may be interoperable with other ECG devices, but they may be exclusive to a hardware sensor and/or sensor component relied upon to generate the data.

Still referring to FIG. 1, static time series image may include multiple time series each with separate domain protocol formats. Specifically, processor 104 may receive static time series image that may include a first time series and a second time series; each of first time series and second time series may include time-series data pertaining to the same category of process being measured, such as time-series data from the same type of diagnostic process or the like. In an embodiment, first time series may be recorded by and/or received from a first device while second time series may be recorded by and/or received from a second device; first device and second device may be different devices and/or different types of devices and may record using the same initial domain protocol as each other or may record in two distinct initial domain protocols. Initial time series data may include a plurality of sets of time series data from a plurality of devices, of which any two devices may include a first device and second device as described above; such initial time series data may include datasets in a plurality of distinct initial domain protocols. As a non-limiting example, multiple ECG data sets, which may be recorded with multiple initial domain protocols, may be used as static time series image to develop a single common protocol for the data sets from each ECG as described in further detail below. Conversion of initial domain protocols to a common protocol may enable a medical professional to use any or all such datasets within either or both hardware configurations to analyze the ECG data. Development of a common domain protocol may be used to support future conversions.

With continued reference to FIG. 1, static time series image may be received through a network of connected devices. In a non-limiting embodiment, a device that captures one or more elements of time series data and/or performs one or more steps described in this disclosure may be communicatively connected to one or more other devices, including without limitation any devices described in this disclosure, a local area network (LAN), a wide area network (WAN) such as the Internet or a subset thereof, such that all recorded data may be accessible via any other web enabled device. In this way, static time series image may be requested and imported into processor 104 via web or local network interface. Processor and/or another device may divide processing tasks between multiple processors to accelerate delivery of completed dynamic time series data.

With continued reference to FIG. 1, static time series image may be received through a direct file importing process, wherein static time series image may be saved and downloaded to processor 104. This may include file transfers from any type of hard drive or other memory type exchange or replication. Static time series image may be locally generated in cases where processor 104 is built in conjunction with or contained within an ECG-capable device. Static time series image may also be imported into processor 104 through manual generation, wherein a user populates all necessary data by any mechanism wherein the minimum required set of time series data is made available to apparatus 100.

With continued reference to FIG. 1, static time series image may be received from a scanning device. In cases where the time series data is only available in a tangible, paper format, the image may be scanned in using any scanner with sufficient clarity in its scanning process. Processor 104 may allow for direct ingestion of the scanned time series image or may support a conversion to a preferred image format. Scanning of the time series image may be accomplished in any manner capable of generating a digital representation of the time series image to include mobile phone image scans, drum scanner scans, flatbed scans, or others.

Still referring to FIG. 1, processor 104 may rely on optical character recognition or optical character reader (OCR), executed by processor 104 to automatically convert images of written (e.g., typed, handwritten or printed) text into machine-encoded text. In some cases, recognition of at least a keyword from an image component may include one or more processes, including without limitation optical character recognition, optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyzes a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases, a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning processes like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIG. 5 below. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool includes OCRopus. OCRopus development is led by German Research Centre for Artificial Intelligence in Kaiserslautern, Germany. In some cases, OCR software may employ neural networks, for example neural networks as taught in reference to FIGS. 6-7 below.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make use of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

Still referring to FIG. 1, image recognition and processing may build upon the character recognition methods discussed above. Time series data is generally less complex to interpret than the infinite possible image types, so a predefined analysis which targets time series types of data may be efficiently translated to an interrogable format, such that the image data may have numerical statistics applied and an underlying algorithm to define the time series graph. As used herein, an "interrogable" format is a format in which the individual data points that make up the time series are both quantified and accessible by processor 104 and the user for processing and analysis. For instance, and without limitation, an interrogable format may permit processor 104 and/or a user to isolate a specific data point such as a value at a set time, a sample number, the sample rate used, or any numeric value associated with any part of the time series. As a further example, in an interrogable format, time series data be possible to be retrieved and/or analyzed using indices, similarly to a vector or array data structure. Interrogable format may alternatively or additionally permit retrieval of entries according to times, which may map to indices and/or act as a substitute therefor. Alternatively or additionally, interrogable format may be configured to permit retrieval of time and/or indices of entries having specified values and/or falling into a range of specified values. As a further alterative or additional example, interrogable format may be configured to retrieve indices, times, values, and/or ranges of values corresponding to peaks, troughs, system and/or user-entered threshold values, first, second, or higher-order derivatives of curves and/or linearized and/or localized approximations thereof, or any other mathematical or other characteristic of a curve or other graphical object represented in interrogable format. Alternatively or additionally, an interrogable format may be a format that can return a set of values belonging to a range, such as a range of values over a period of a periodic signal, a range of values over a fraction of a period such as a half-period, quarter-period, or the like, a range of values found between two consecutive specified points as described above, including between two peaks, troughs, zeros, zeros of first, second, or higher-order derivatives, or the like. As an additional example, interrogable format may permit and/or be configured to perform retrieval of samples from a portion of a graph and/or signal that matches a particular pattern, such as a pattern representing a specific cardiac event such as a "heart murmur," Q-waves, delta waves, Brugada syndrome signal elements, QRS-end slurring and/or notching, Digoxin effects, arrythmias, and/or other elements of interest in analysis of a signal. Pattern matching may be performed, without limitation, using a classifier, which may include any classifier as described in this disclosure. Classifier may be trained using training data correlating sequences of samples with matching sequences of samples and/or labels as entered, for instance, by an expert user such as a medical provisional; in some embodiments, a query may include a sequence to be matched with sequences within a signal in interrogable format, while in other embodiments query may include a label, for instance by way of classifying different sequences within interrogable signal to labels that can then be matched to queries containing similar labels. Any or all of the data structures and/or elements used for retrieval may be a part of a data structure instantiating interrogable format and/or may be maintained and/or utilized separately on apparatus or other devices. Interrogation of time series data may further support additional analysis including medical diagnoses, outlier erred data, or other identifiable information from the quantified dataset. Translation of the raw image into a numerically defined time series format may rely and/or include optical character recognition described above to interpret axes and/or labels of data. With the axes and/or labels defined, time series numerical characteristics may be applied based on the timing and relative locations of peaks and troughs, consistency of the waveform, amplitudes, and any other identifiable features.

Still referring to FIG. 1, processor 104 is configured to convert at least a static time series image to a dynamic time series dataset within a target domain protocol. Conversion of the static time series image to a dynamic time series data may use an unsupervised generative machine-learning process. As used in this disclosure, a "target domain protocol" is a domain protocol to which data received in one or more initial domain protocols is converted; target domain protocol may be a distinct domain protocol from each initial domain protocol or may be one of a plurality of initial domain protocols. Where two or more domain protocols exist for a given category of time-series data, target domain protocol may serve as a common domain protocol into which all other domain protocols may be converted, for instance and without limitation permitting use of all such converted datasets as training data and/or inputs for a machine-learning model, display of all such converted datasets at or by a given device that can accept and/or display data using target domain protocol, or the like. As used herein, a "common domain protocol" is a selected protocol to which all the different domains are translated so they can be used together in a process such as a machine-learning process. While a common domain protocol may not be a required transition for all time series conversions, in many cases it may allow for a standardized conversion process and gain efficiency within processor 104 operations. In some embodiments, processor 104 may be used to generate a universal common domain such that the common domain may act as the target domain and/or be used as real example. Use of a common domain may allow for an immediate conversion of all time series data sets immediately after generation such that all data of a specific type may be collocated and compatible within the common domain. A common domain time series data may then either be converted to a separate, user-specified target domain by repetition of processes for conversion as described in this disclosure, or it may be used as it exists in the common domain format. In this way, a common domain implementation may be used as an intermediary interpretation, to enable the comparing and contrasting of multiple sources of time series data, while also simplifying the conversion from the common domain to the various target domains. Use of a common domain protocol may simplify various conversions by converting from thousands of device domains to a single, unitary domain format.

With continued reference to FIG. 1, further disclosure regarding converting a static image to ECG data 110 may be found in U.S. Nonprovisional application Ser. No. 18/591,499, filed on Feb. 29, 2024, and entitled "APPARATUS AND METHOD FOR TIME SERIES DATA FORMAT CONVERSION AND ANALYSIS," U.S. Nonprovisional application Ser. No. 18/641,217, filed on Apr. 19, 2024, and entitled "SYSTEMS AND METHODS FOR TRANSFORMING ELECTROCARDIOGRAM IMAGES FOR USE IN ONE OR MORE MACHINE LEARNING MODELS," and U.S. Nonprovisional application Ser. No. 18/652,364, filed May 1, 2024, and entitled "Apparatus and Method for Training a Machine Learning Model to Augment Signal Data and Image Data," the entirety of each of which is incorporated herein by reference.

With continued reference to FIG. 1, memory 106 may include instructions configuring the at least a processor 104 to receive ECG data 110 from ECG device 108. In some embodiments, processor 104 may receive ECG data 110 through a wired connection. A wired connection, as non-limiting examples, may include ethernet, coax, USB, TRS, HDMI, RCA, XLR, component, and the like. In some embodiments, processor 104 may receive ECG data 110 through a wireless connection. A wireless connection, as non-limiting examples, may include WiFi, radio, NFC, BlueTooth, Cellular data, 2G, 3G, 4G, LTE, 5G, and the like.

With continued reference to FIG. 1, processor 104 and/or computing device 102 may be communicatively connected ECG device 108. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 106 includes instructions configuring the at least a processor 104 to generate, using a repeat-ablation efficacy machine-learning model 113, repeat ablation efficacy data 115 representing predicted efficacy of a repeat ablation procedure. In some embodiments, repeat ablation procedure may be to resolve an arrhythmia of patient 112. For the purposes of this disclosure, a "repeat ablation procedure" is an ablation procedure that is performed on a patient that has already undergone at least another ablation procedure.

With continued reference to FIG. 1, in some embodiments, repeat-ablation efficacy machine-learning model 113 may be configured to receive as input post-ablation arrhythmic ECG data. In some embodiments, processor 104 may be configured to input, into repeat-ablation efficacy machine-learning model 113, post-ablation arrhythmic ECG data.

With continued reference to FIG. 1, in some embodiments, repeat-ablation efficacy machine-learning model 113 may be configured to output repeat-ablation efficacy data 115. In some embodiments, processor 104 may be configured to receive as output, from repeat-ablation efficacy machine-learning model 113, repeat-ablation efficacy data 115.

With continued reference to FIG. 1, in some embodiments, repeat-ablation efficacy data 115 may include a quantitative value. For example, quantitative value may include a probably. For example quantitative value may include a probability that a recurrent case of Afib may be addressed through a repeat ablation procedure. In some embodiments, repeat-ablation efficacy data may be a quantitative value, such as "good," "bad," "ok," and the like. In some embodiments, repeat-ablation efficacy data may include a classification. In some embodiments, classification may be based on the relative likelihood of success of a repeat ablation procedure. In some embodiments, classification may include a suggested next treatment.

With continued reference to FIG. 1, repeat-ablation efficacy machine-learning model 113 may include, as non-limiting examples, treatment machine-learning model 136 and/or ablation evaluation machine-learning model 114.

With continued reference to FIG. 1, repeat-ablation efficacy machine-learning model 113 may be trained using ablation training data. In some embodiments, ablation training data may be retrieved from an EHR database 120. In some embodiments, ablation training data may include historical electrocardiogram data correlated to historical ablation data. In some embodiments, historical ablation data may include historical repeat ablation efficacy data. In some embodiments, ablation training data may be de-identified consistent with other training data in this disclosure.

With continued reference to FIG. 1, memory 106 includes instructions configuring the at least a processor 104 to generate, using an ablation evaluation machine-learning model 114, ablation evaluation data 118 of patient 112. For the purposes of this disclosure, "ablation evaluation data," is data related an evaluation of pulmonary vein reconnection. For example, ablation evaluation data 118 may include a predicted likelihood of pulmonary vein reconnection. E.g., 10%, 20%, 50%, and the like. Ablation evaluation data may include detecting whether or not there are pulmonary vein reconnections. This may be undesirable as it may cause certain medical issues of patient 112 to begin to reoccur, such as atrial fibrillation. Thus accurate ablation evaluation data 118 may allow for detection of patients 112 wherein medical issues are likely to reoccur. Ablation evaluation machine-learning model 114 may be consistent with any machine-learning model disclosed in this disclosure. In some embodiments, ablation evaluation machine-learning model 114 may be created using a machine-learning module, such as machine-learning module 300 disclosed with reference to FIG. 3.

With continued reference to FIG. 1, memory 106 contains instructions configuring processor 104 to train an ablation evaluation machine-learning model 114 using ablation evaluation training data 116. Ablation evaluation training data 116 may include historical ECG data 110 correlated to historical ablation evaluation training data 116. In some embodiments, ablation evaluation training data 116 may be retrieved from a database. In some embodiments, ablation evaluation training data 116 may be retrieved from an electronic health record (EHR) database 120.

With continued reference to FIG. 1, an "electronic health record database," for the purposes of this disclosure, is a database that contains digital information concerning one or more patients' medical history. EHR database 120 may store one or more patient's EHR. An "electronic health record," for the purposes of this disclosure is a digital record of a patient's health history. An EHR may include a digital system for storing patient and population health information in a standardized format, enabling easy sharing across various healthcare settings. EHRs may encompass a wide range of data, including patient demographics, medical history, medications, allergies, immunization records, lab results, radiology images, vital signs, and billing details. They may enhance healthcare quality by providing comprehensive data for care management programs, facilitating the development of new treatments, and improving healthcare delivery. EHRs may ensure accurate, up-to-date, and legible records, reduce the risk of data replication, and promote better communication between patients and providers. Additionally, EHRs may support population-based studies by enabling efficient data extraction and analysis of long-term patient trends.

With continued reference to FIG. 1, databases, as described in this disclosure, may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, in some embodiments, EHR database 120 may be located remotely from computing device 102. For example, in some embodiments, EHR database 120 may be located in the cloud. In some embodiments, EHR database 120 may be located locally at computing device 102.

With continued reference to FIG. 1, "training data," as used in this disclosure, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by processor 104 may correlate any input data as described in this disclosure to any output data as described in this disclosure.

With continued reference to FIG. 1, memory 106 contains instructions configuring processor 104 to generate ablation evaluation training data 116. In some embodiments, generating ablation evaluation training data 116 may include retrieving historical ECG data 110 correlated to historical ablation performance data 124. "Historical ECG data," for the purposes of this disclosure, is ECG data that has been collected in the past and not from a current patient. "Historical ablation performance data," for the purposes of this disclosure, is ablation performance data relating to past users and patient, not a current patient.

With continued reference to FIG. 1, in some embodiments, processor 104 may be configured to receive ablation evaluation training data 116 from EHR database 120. In some embodiments, historical ECG data 110 may be received from EHR database 120. In some embodiments, historical ablation performance data 124 may be received from EHR database 120.

With continued reference to FIG. 1, in some embodiments, training ablation evaluation machine-learning model 114 may include receiving a plurality of patient health records 126 from EHR database 120. A "patient health record," for the purposes of this disclosure is a record of the medical history of a patient. In some embodiments, processor 104 may be configured to identify a subset of patient health records 128 from an EHR database 120. In some embodiments, subset of patient health records 128 may be a subset of patient health records 128. Processor 104 may be configured to identify a subset of patient health records 128 comprising post-ablation ECG data 130. For the purposes of this disclosure, "post-ablation ECG data" is data of one or more electrocardiograms that were performed on patients after they have undergone an ablation procedure.

With continued reference to FIG. 1, identifying subset of patient health records 128 may include using natural language processing. In some embodiments, this may include using a language processing module. Language processing module may include any hardware and/or software module. Language processing module may be configured to extract, from the one or more documents, one or more words. One or more words may include, without limitation, strings of one or more characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module may operate to produce a language processing model. Language processing model may include a program automatically generated by computing device and/or language processing module to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

Still referring to FIG. 1, language processing module and/or diagnostic engine may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Alternatively or additionally, and with continued reference to FIG. 1, language processing module may be produced using one or more large language models (LLMs), neural networks, and the like.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module may use a corpus of documents to generate associations between language elements in a language processing module, and diagnostic engine may then use such associations to analyze words extracted from one or more documents and determine that the one or more documents indicate significance of a category. In an embodiment, language module and/or processor 104 may perform this analysis using a selected set of significant documents, such as documents identified by one or more experts as representing good information; experts may identify or enter such documents via graphical user interface, or may communicate identities of significant documents according to any other suitable method of electronic communication, or by providing such identity to other persons who may enter such identifications into processor 104. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, diagnostic engine may automatically obtain the document using such an identifier, for instance by submitting a request to a database or compendium of documents such as JSTOR as provided by Ithaka Harbors, Inc. of New York.

With continued reference to FIG. 1, processor 104 may use language processing module to identify patient health records 126 that include post-ablation ECG data 130. For example, processor 104 may use language processing module to detect data elements for each part of a patient health record 126 and, if patient health record 126 contains an ECG procedure that occurs temporally after an ablation procedure. An "ablation procedure," for the purposes of this disclosure, is a medical procedure that involves removing or destroying tissue within the body. Ablation procedures may include, as non-limiting examples, radiofrequency ablation, cryoablation, maze ablation, laser ablation, heat ablation, pulsed-field ablation (PFA), and the like.

With continued reference to FIG. 1, in some embodiments, processor 104 may be configured to identify subset of patient health records 128 containing post-ablation ECG data 130 using a patient health record classifier. Patient health record classifier may be consistent with any classifier disclosed in this disclosure. Patient health record classifier may be trained using health record training data. Health record training data may include inputs correlated to outputs. Health record training data may include examples of patient health records 126 labeled according to whether they contain post-ablation ECG data 130. In some embodiments, health record training data may be labeled by medical experts.

With continued reference to FIG. 1, "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 102 and/or another device may generate a classifier using a classification algorithm, defined as a processes whereby a computing device 102 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 102 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)+P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 102 may then calculate a likelihood table by calculating probabilities of different data entries and classification labels. Computing device 102 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 102 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 1, processor 104 may be configured to further process subset of patient health records 128 to filter out patient health records 126 wherein the ECG occurred outside of a time window after the ablation procedure. For example, time window may be 1 week, 2 weeks, 1 month, 2 months, 3 months, 6 months, 8 months, 1 year, or 2 years. Time window may, in some embodiments, be between 1 day and 3 years. Time window may, in some embodiments, be between 1 day and 2 years. Time window may, in some embodiments, be between 1 month and 2 years.

With continued reference to FIG. 1, in some embodiments, historical ablation performance data 124 may be manually assigned for each patient health record 126 (or, subset of patient health records 128) by a medical professional. In some embodiments, historical ablation performance data 124 may be identified using a language processing module as discussed above. In some embodiments, language processing module may identify keywords associated with ablation outcomes and use those keywords to identify historical ablation performance data 124 within patient health records 126 (or, subset of patient health records 128).

With continued reference to FIG. 1, processor 104 may generate ablation evaluation training data 116 from subset of patient health records 128. In some embodiments, processor 104 may use subset of patient health records 128 as ablation evaluation training data 116.

With continued reference to FIG. 1, processor 104 may be configured to train ablation evaluation machine-learning model 114 using ablation evaluation training data. In some embodiments, this may be an iterative process, wherein ablation evaluation machine-learning model is trained and retrained until it surpasses an accuracy threshold. In some embodiments, ablation evaluation machine-learning model 114 may be periodically retrained with updated training data. In some embodiments, ablation evaluation machine-learning model may be retrained using feedback.

With continued reference to FIG. 1, in some embodiments, generating ablation evaluation training data 116 from subset of patient health records 128 may include de-identifying the subset of patient health records. For the purposes of this disclosure, "de-identifying the subset of patient health records" is removing personally identifying information (PII) from the patient health records. "PII," for the purposes of this disclosure, is any information that can be used to identify, contact, or locate and individual, either directly or indirectly. Processor 104 may be configured to identify, using language processing module, one or more instances of PII within patient health records 126. In some embodiments, processor 104 may be configured to replace these instances of PII with generic placeholders such as, for a name, "[NAME]" or "John," or, for a birthday, MMD-DYYY, and the like. In some embodiments, processor 104 may be configured to, before replacing instances of PII with generic placeholders, identify false positives using a false positives list. False positives list may include a plurality of terms or tokens that, while they may resemble PII, actually are not. For example, the word Heimlich (for the Heimlich maneuver) may be incorrectly identified as PII because it is also a last name; however, Heimlich may be on the false positives list and then processor 104 may mark it as non PII so that it does not get replaced with a generic placeholder.

With continued reference to FIG. 1, memory 106 contains instructions configuring processor 104 to input, into ablation evaluation machine-learning model 114, ECG data 110. Ablation evaluation machine-learning model may be configured to receive ECG data 110 as input and output ablation evaluation data 118. Memory 106 contains instructions configuring processor 104 to receive, as output, from ablation evaluation machine-learning model 114, ablation evaluation data 118 of patient 112.

With continued reference to FIG. 1, in some embodiments, ablation evaluation data 118 may include predicted chance 132 of pulmonary vein reconnection. For the purposes of this disclosure, a "predicted chance of pulmonary vein reconnection" is a likelihood that a pulmonary vein of a patient will reconnect with the atria. In some embodiments, predicted chance 132 of pulmonary vein reconnection may include quantitative data, such as a percent chance. In some embodiments, predicted chance 132 of pulmonary vein reconnection may include qualitative data, such as descriptors like "likely," "very likely," "unlikely," "very unlikely," "neutral," and the like. In some embodiments, ablation evaluation training data may include historical ECG data 110 correlated to predicted chances 132 of pulmonary vein reconnection.

With continued reference to FIG. 1, in some embodiments, memory 106 may contain instructions configuring processor 104 to determine a treatment recommendation 134. A "treatment recommendation," for the purposes of this disclosure, is a suggestion of an optimal treatment for a patient.

With continued reference to FIG. 1, in some embodiments, memory 106 may contain instructions configuring processor 104 to generate, using a treatment machine-learning model 136, treatment recommendation 134 as a function of ECG data 110. In some embodiments, treatment machine-learning model 136 may be configured to receive ECG data 110 as input. In some embodiments, treatment machine-learning model 136 may be configured to output treatment recommendation 134. In some embodiments, treatment machine-learning model 136 may be configured to receive both ECG data 110 and ablation evaluation data 118 as input. Treatment machine-learning model 136 may be consistent with any machine-learning model disclosed in this disclosure. In some embodiments, treatment machine-learning model 136 may be created using a machine-learning module, such as machine-learning module 300 disclosed with reference to FIG. 3.

With continued reference to FIG. 1, memory 106 may contain instructions further configuring processor 104 to receive treatment training data 138. In some embodiments, receiving treatment training data 138 may include receiving treatment training data 138 from a database. In some embodiments, receiving treatment training data 138 may include receiving treatment training data 138 from EHR database 120. In some embodiments, treatment training data may include historical ECG data 110 correlated to historical treatment data 140. "Historical treatment data," for the purposes of this disclosure are historical records of treatments assigned to patients. In some embodiments, memory 106 may contain instructions configuring processor 104 to train treatment machine-learning model 136 using the treatment training data 138. In some embodiments, memory 106 may contain instructions configuring processor 104 to generate treatment recommendation 134 using trained treatment machine-learning model 136.

With continued reference to FIG. 1, in some embodiments, treatment recommendation 134 may include a secondary ablation target 142. For the purposes of this disclosure, a "secondary ablation target" is an ablation target for a second ablation procedure, wherein the second ablation procedure is additional to the ablation procedure that a patient has already undergone. A "primary ablation target," for the purposes of this disclosure, is the ablation target for the ablation procedure that the patient has already undergone. Primary ablation target may include pulmonary vein. In some embodiments, secondary ablation target 142 may be the same as primary ablation target. In some embodiments, secondary ablation target 142 may be pulmonary vein. In some embodiments, secondary ablation target 142 may be different from primary ablation target. As non-limiting examples, secondary ablation target 142 may include superior vena cava or posterior wall. In some embodiments, treatment training data 138 may include historical ECG data 110 correlated to historical secondary ablation targets 142.

With continued reference to FIG. 1, memory 106 may contain instructions configuring processor 104 to receive post-recommended treatment ECG 144. A "post-recommended treatment ECG," for the purposes of this disclosure, is ECG data from an ECG on the patient that was conducted after the treatment recommendation was carried out. In some embodiments, processor may retrieve post-recommended treatment ECG 144 from EHR database 120.

With continued reference to FIG. 1, memory 106 may contain instructions configuring processor 104 to receive recommended treatment outcome data 146. For the purposes of this disclosure, "recommended treatment outcome data" is data concerning the outcome of the recommended treatment. In some embodiments, processor may retrieve recommended treatment outcome data 146 from EHR database 120. In some embodiments, recommended treatment outcome data 146 may include qualitative data concerning the relative success of the procedure. In some embodiments, recommended treatment outcome data 146 may include quantitative data on the relative success of the procedure. In some embodiments, recommended treatment outcome data 146 may include binary data on the success or failure of the procedure. For example, a "1" may indicate success while a "0" indicates failure.

With continued reference to FIG. 1, memory 106 may contain instructions configuring processor 104 to retrain treatment machine-learning model 136 as a function of post-recommended treatment electrocardiogram 144 and recommended treatment outcome data 146. For example, post-recommended treatment electrocardiogram 144 and recommended treatment outcome data 146 may be correlated together and used as a training pair when treatment machine-learning model 136 is retrained.

With continued reference to FIG. 1, memory 106 may contain instructions configuring processor 104 to receive ablation data 148 from ablation device 150. An "ablation device," for the purposes of this disclosure, is a device that is configured to perform an ablation procedure. In some embodiments, ablation device may include a catheter. In some embodiments, ablation device may include a radiofrequency ablation device. In some embodiments, ablation device may include a cryoablation device. In some embodiments, ablation device may include a PFA ablation device.

With continued reference to FIG. 1, "ablation data," for the purposes of this disclosure, is data concerning an ablation procedure. In some embodiments, ablation data 148 may include parameter data for ablation device. In some embodiments, ablation data 148 may include data concerning the pulse strength and/or duration for the ablation procedure. In some embodiments, ablation data 148 may include an ablation durability.

With continued reference to FIG. 1, further discussion of ablation data and ablation durability may be found in U.S. Non-provisional application Ser. No. 18/671,644, filed on May 22, 2024, and entitled "SYSTEMS AND METHODS FOR DETERMINING DOSAGE PARAMETERS TO ENSURE DURABILITY IN TREATMENT PROCESSES," and U.S. Non-provisional application Ser. No. 18/646,991, filed on Apr. 26, 2024, and entitled "METHOD AND APPARATUS FOR PREDICTING PULSED FIELD ABLATION DURABILITY," the entirety of each of which is incorporated herein by reference.

With continued reference to FIG. 1, in some embodiments, ablation evaluation machine-learning model 114 may be configured to receive ablation data 148 and ECG data 110 as input and output ablation evaluation data 118. In some embodiments, ablation evaluation training data 116 may include historical ECG data 110 and historical ablation data 148 correlated to historical ablation performance data 124. In some embodiments, historical ablation data 148 may be retrieved from EHR database 120.

With continued reference to FIG. 1, apparatus 100 may further include a display device 152. Display device 152 may be configured to display a user interface 154 which may be configured to receive one or more inputs from a user. In some embodiments, processor 104 may be configured to generate user interface 154. In some embodiments, processor 104 may be configured to display ablation evaluation data 118 using display device. In some embodiments, processor 104 may be configured to display treatment recommendation 134 using display device 152. A "display device," for the purposes of this disclosure, is an electronic device configured to display visual data to a user. Display device 152 may include various screens, such as, as non-limiting examples, OLED, LCD, LED, CRT, QLED, plasma, and the like. Display device 152 may include a monitor, television, projector, and the like.

With continued reference to FIG. 1, in some embodiments, processor 104 may be configured to transmit, for display, repeat-ablation efficacy data 115 In some embodiments, processor 104 may be configured to display repeat-ablation efficacy data 115.

With continued reference to FIG. 1, in some embodiments, apparatus 100 may include a catheter 156. A "catheter," for the purposes of this disclosure, is a flexible tube that is configured to be inserted into the body. In some embodiments, catheter 156 may include a mapping catheter. A "mapping catheter," for the purposes of this disclosure, is a catheter that is configured to map human anatomy. Mapping catheter may include electrophysiology (EP) mapping catheter. In some embodiments, catheter 156 may include an ablation catheter. In some embodiments, ablation device 150 may include an ablation catheter. An "ablation catheter," for the purposes of this disclosure, is a catheter that is configured to ablate tissue within the body. In some embodiments, ablation catheter may include a radio-frequency ablation catheter. In some embodiments, ablation catheter may include a cryoablation catheter. In some embodiments, ablation catheter may include a pulsed field ablation (PFA) catheter. In some embodiments, ablation catheter may include an electrode configured to apply electric pulses to tissue. In some embodiments, electrode may be configured to apply various ablation parameters, such as pulse width, pulse frequency, pulse mode, voltage amplitude, number of pulses, interphase, and/or interpulse delay. In some embodiments, ablation data 148 may include ablation parameters as discussed above.

With continued reference to FIG. 1, in some embodiments, apparatus 100 may receive intracardiac echocardiogram (ICE) data 158. For the purposes of this disclosure, ICE data 158 is data collected from an ultrasound probe that is inserted into the heart of a patient. In some embodiments, ICE data 158 may be collected using a catheter 156, such as in ICE catheter.

With continued reference to FIG. 1, in some embodiments, processor 104 may be configured to receive ICE data 158, ablation data 148, ECG data 112, catheter data, ultrasound data, and/or CT data. In some embodiments, repeat-ablation efficacy machine-learning model 113 may be configured to receive ICE data 158, ablation data 148, catheter data, ultrasound data, and/or CT data as input. In some embodiments, repeat-ablation efficacy machine-learning model 113 may include models configured to process each mode of input data and output ablation efficacy data 115. In some embodiments, repeat-ablation efficacy machine-learning model 113 may include one or more multimodal models, wherein a multimodal model may be configured to receive as input multiple modes of data at once. In some embodiments, multimodal model may include a multimodal transformer.

With continued reference to FIG. 1, ablation training data may include historical electrocardiogram data 112 correlated to historical ablation data. In some embodiments, ablation training data may include historical ICE data, historical ECG data 112, historical ablation data, historical catheter data, historical ultrasound data, and/or historical CT data correlated to historical ablation data. In some embodiments, treatment training data 138 may include historical ICE data, historical ECG data 112, historical ablation data, historical catheter data, historical ultrasound data, and/or historical CT data correlated to historical treatment data 140. In some embodiments, ablation evaluation training data 116 may include historical ICE data, historical ECG data 112, historical ablation data, historical catheter data, historical ultrasound data, and/or historical CT data correlated to historical ablation performance data 124. In some embodiments, historical ICE data, historical ECG data 112, historical ablation data, historical catheter data, historical ultrasound data, and/or historical CT data may include historical prior-procedure data, wherein historical prior-procedure data is data collected during or temporally adjacent to a prior ablation procedure of a historical patient.

With continued reference to FIG. 1, ICE data 158 may include prior-procedure ICE data. "Prior-procedure ICE data," for the purposes of this disclosure, is data collected from an ICE of a patient, wherein the collected during or temporally adjacent to a prior ablation procedure of the patient. In some embodiments, processor 104 may be configured to receive prior-procedure ICE data. In some embodiments, processor 104 may be configured to generate repeat-ablation efficacy data 115 by inputting prior-procedure ICE data into repeat-ablation efficacy machine-learning model 113.

With continued reference to FIG. 1, in some embodiments, ablation data 148 may include prior-procedure ablation data. "Prior-procedure ablation data," for the purposes of this disclosure, is data collected from an ablation of a patient, wherein the collected during or temporally adjacent to a prior ablation procedure of the patient. In some embodiments, processor 104 may be configured to receive prior-procedure ablation data. In some embodiments, processor 104 may be configured to generate repeat-ablation efficacy data 115 by inputting prior-procedure ablation data into repeat-ablation efficacy machine-learning model 113.

Figure 2:
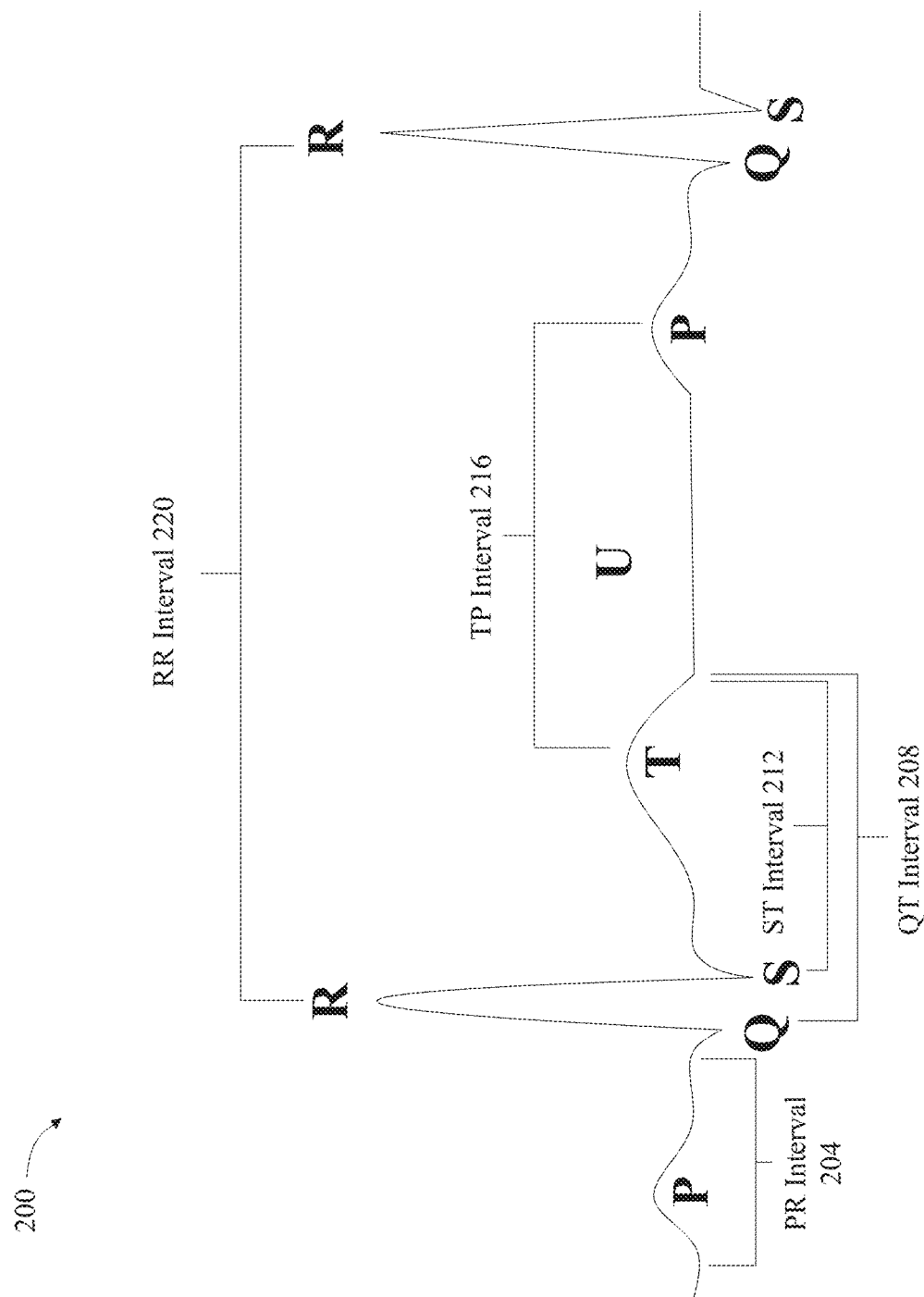
FIG. 2 illustrates an exemplary embodiment of an ECG.

Referring now to FIG. 2, an exemplary embodiment of ECG 200 is illustrated. ECG may include a plurality of features such as P-wave, Q-wave, R-wave, S-wave, QRS complex, and T wave, as well as a plurality of parameters such a PR interval 204, QT interval 208, ST interval 212, TP interval 216, RR interval 220, and the like. P-wave may reflect atrial depolarization (activation). For the purposes of this disclosure, a "PR interval" is the distance between the onset of P-wave to the onset of QRS complex. PR interval 204 may be assessed to determine whether impulse conduction from the atria to the ventricles is normal. PR interval 204 may be measured in seconds. For the purposes of this disclosure, a "QT interval" is a reflection of the total duration of ventricular depolarization and repolarization and is measured from the onset of QRS complex to the end of T-wave. The QT duration may be inversely related to heart rate; i.e., QT interval 208 may increase at slower heart rates and decrease at higher heart rates. Therefore, to determine whether QT interval 208 is within normal limits, it may be necessary to adjust for the heart rate. A heart rate-adjusted QT interval 208 is referred to as a corrected QT interval 208 (QTc interval). A long QTc interval may indicate an increased risk of ventricular arrhythmias. The QTc interval may be in the range of 0.36 to 0.44 seconds. For the purposes of this disclosure, an "RR interval" is the time between two consecutive R waves. For the purposes of this disclosure, a "QRS complex" is a representation of the depolarization (activation) of ventricles depicted between Q-, R- and S-waves, although it may not always display all three waves. Since the electrical vector generated by the left ventricle is usually many times larger than the vector generated by the right ventricle, QRS complex is a reflection of left ventricular depolarization.

With continued reference to FIG. 2, for the purposes of this disclosure, an "ST interval" is the segment of ECG that starts at the end of QRS complex and extends to the beginning of T wave; it represents the early part of ventricular repolarization. ST segment may be relatively isoelectric, meaning it is at the baseline, with minimal elevation or depression. The normal duration of ST interval 212 is usually around 0.12 seconds. For the purposes of this disclosure, a "TP interval" is the segment of ECG that extends from the end of T wave to the beginning of the next P wave; it represents the time when the ventricles are fully repolarized and are in a resting state. The duration of TP interval 216 may vary but is typically short, as it may represent the brief pause between cardiac cycles. Significant deviations may be associated with certain conditions affecting repolarization. For the purposes of this disclosure, an "RR interval" is the time between two consecutive R waves of ECG; it may represent the duration of one cardiac cycle, encompassing both atrial and ventricular depolarization and repolarization. RR interval 220 may be measured in seconds and can be used to calculate heart rate (beats per minute) using $$\text{heart rate} = \frac{60}{RR \text{ Interval}} (\text{in seconds}).$$

The intervals described above may be used to determine a ventricular rate, i.e., the number of ventricular contractions (heartbeats) that occur in one minute, which may be closely related to RR interval 220 of ECG, as the RR interval 220 represents the time between two consecutive ventricular contractions.

Figure 3:
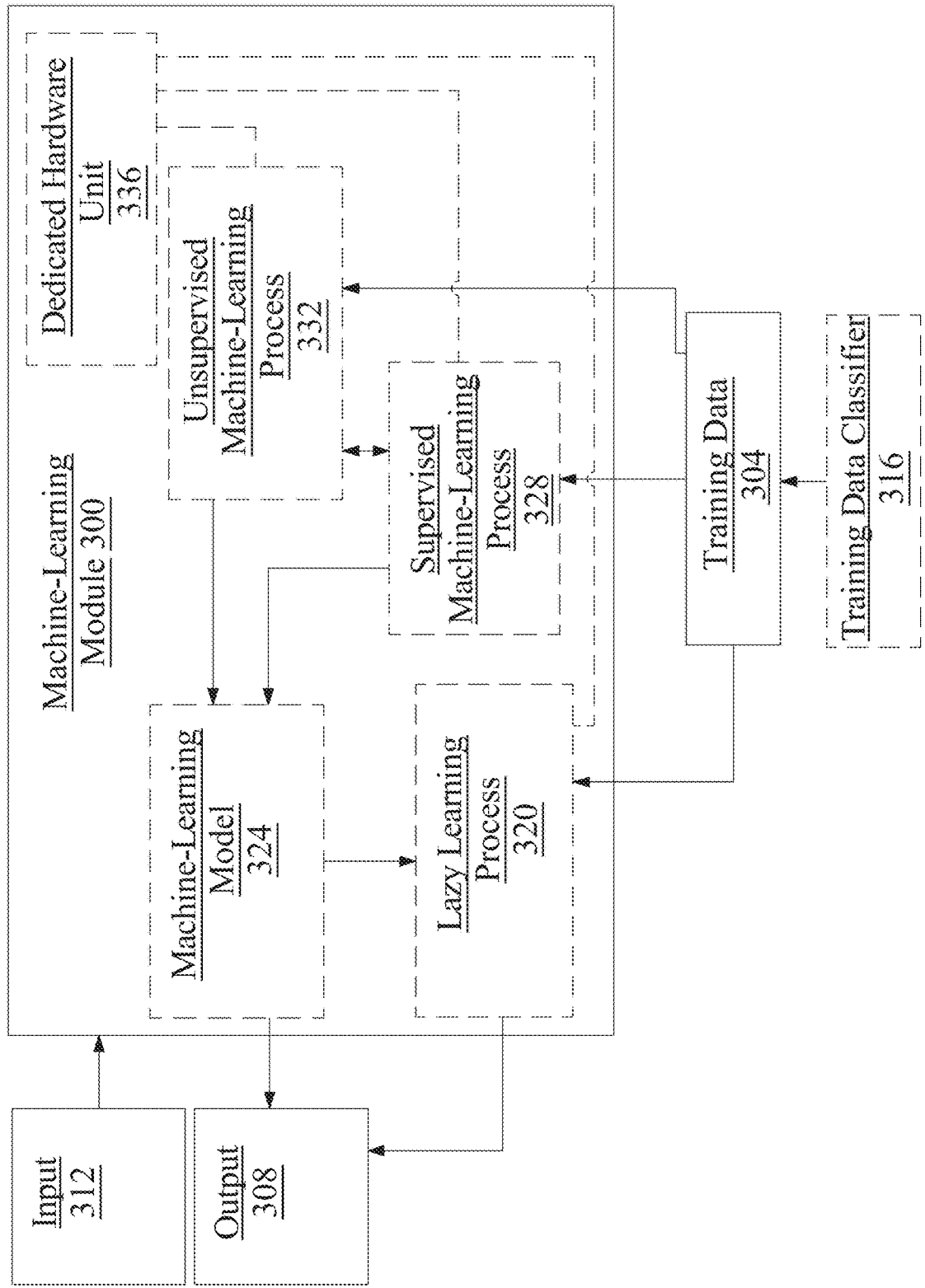
FIG. 3 is a block diagram of an exemplary embodiment of a machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example historical ECG data and historical ablation performance data.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to patient sex, patient age, patient medical history, whether or not the patient has already had an ablation procedure, and the like.

Still referring to FIG. 3, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)+P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 3, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 3, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 3, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels.

It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 3, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $X_{max}$:

$$X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 3, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described above as inputs, outputs as described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 332 may not require a response variable; unsupervised processes 332 may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 3, one or more processes or algorithms described above may be performed by at least a dedicated hardware unit 336. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 336 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
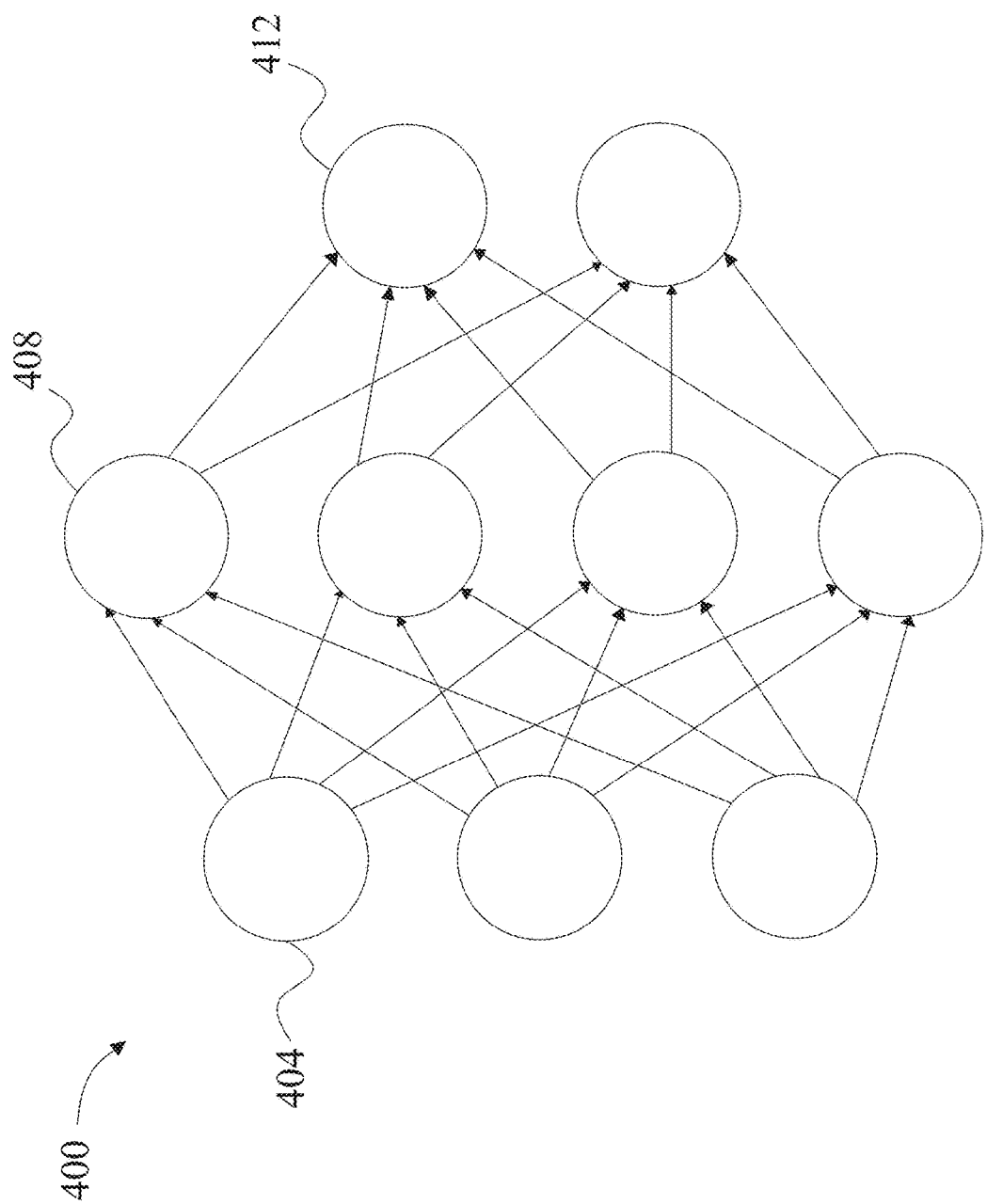
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
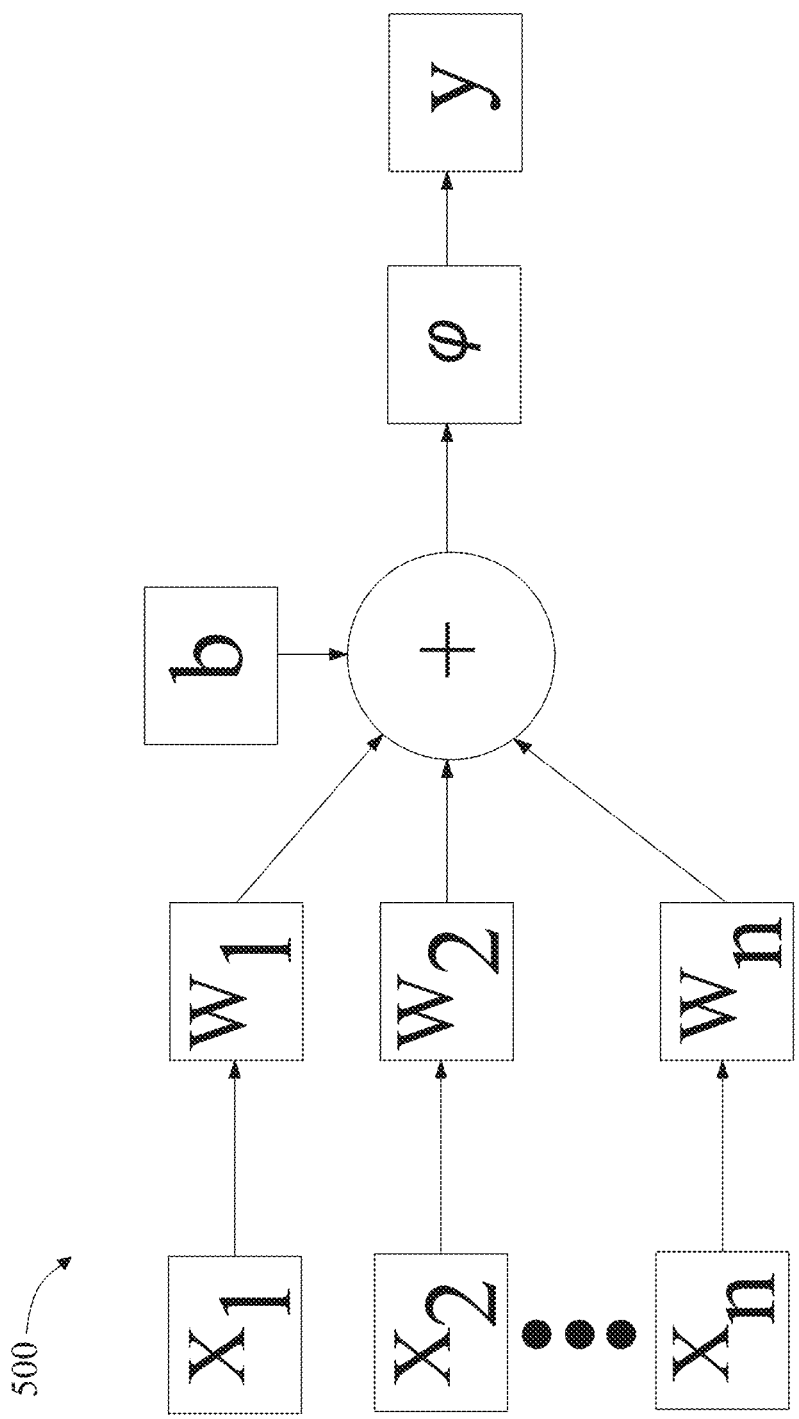
FIG. 5 is a diagram of an exemplary embodiment of a node of a neural network.

Referring now to FIG. 5, an exemplary embodiment of a node 500 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax,x)$ for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x^*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
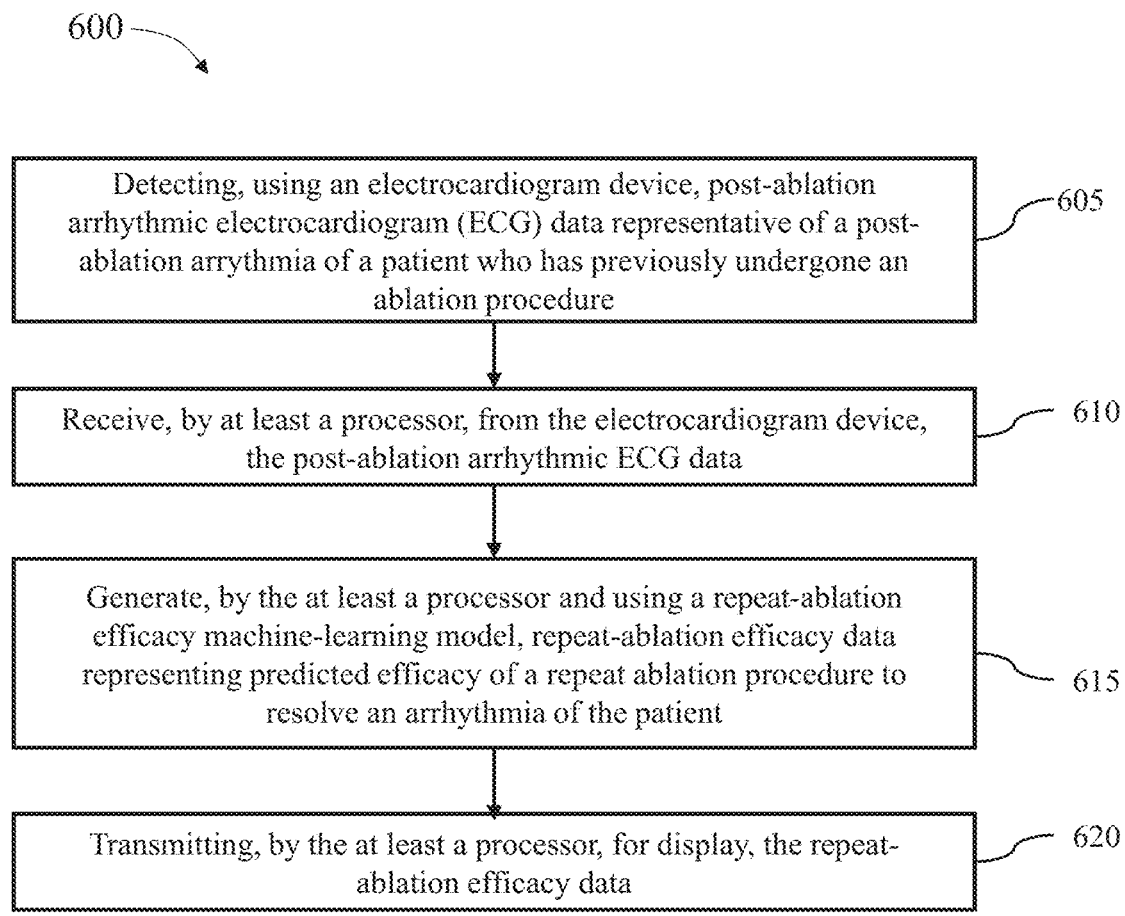
FIG. 6 is a flow diagram illustrating an exemplary method for prediction of pulmonary vein reconnection.

Referring now to FIG. 6, a method 600 for prediction of pulmonary vein reconnection is illustrated. Method 600 includes a step 605 of detecting, using an electrocardiogram device, post-ablation arrhythmic electrocardiogram (ECG) data representative of a post-ablation arrhythmia of a patient who has previously undergone an ablation procedure. In some embodiments, electrocardiogram device may include a 12-lead electrocardiogram device. This may be implemented as disclosed with reference to FIGS. 1-5, without limitation.

With continued reference to FIG. 6, method 600 may include a step of generating, by at least a processor, training data, wherein generating the training data comprises retrieving historical electrocardiogram data correlated to historical ablation data. In some embodiments, step 610 may include receiving a plurality of patient health records from an electronic health record database, identifying a subset of patient health records comprising a post-ablation ECG data, and generating the training data from the subset of patient health records. In some embodiments, step 610 may include de-identifying the subset of patient health records. This may be implemented as disclosed with reference to FIGS. 1-5, without limitation.

With continued reference to FIG. 6, method 600 may include a step of training, by the at least a processor, an repeat-ablation efficacy machine-learning model using the training data. This may be implemented as disclosed with reference to FIGS. 1-5, without limitation.

With continued reference to FIG. 6, method 600 includes a step 610 of receiving, by at least a processor, from the electrocardiogram device, the post-ablation arrhythmic ECG data. This may be implemented as disclosed with reference to FIGS. 1-5, without limitation.

With continued reference to FIG. 6, method 600 includes a step 615 of generating, by the at least a processor and using a repeat-ablation efficacy machine-learning model, repeat-ablation efficacy data representing predicted efficacy of a repeat ablation procedure to resolve an arrhythmia of the patient. Step 625 also includes inputting, into the repeat-ablation efficacy machine-learning model, the post-ablation arrhythmic ECG data. Step 625 also includes receiving as output, from the repeat-ablation efficacy machine-learning model, the repeat-ablation efficacy data. In some embodiments, ablation evaluation data may include a predicted chance of pulmonary vein reconnection. This may be implemented as disclosed with reference to FIGS. 1-5, without limitation.

With continued reference to FIG. 6, method 600 includes a step of 620 of transmitting, by the at least a processor, for display, the repeat-ablation efficacy data. This may be implemented as disclosed with reference to FIGS. 1-5, without limitation.

With continued reference to FIG. 6, method 600 may include a step of determining, by the at least a processor, a treatment recommendation, wherein determining the treatment recommendation comprises generating, using a treatment machine-learning model, a treatment recommendation as a function of the electrocardiogram data. This step may further include receiving treatment training data, wherein the treatment training data comprises historical electrocardiogram data correlated to historical treatment data, training the treatment machine-learning model using the treatment training data, and generating the treatment recommendation using the trained treatment machine-learning model. This may be implemented as disclosed with reference to FIGS. 1-5, without limitation. In some embodiments, method 600 may further include a step of displaying, using a display device, the treatment recommendation. This may be implemented as disclosed with reference to FIGS. 1-5, without limitation. In some embodiments, method 600 may further include a step of receiving, by the at least a processor, a post-recommended treatment electrocardiogram and recommended treatment outcome data. This may be implemented as disclosed with reference to FIGS. 1-5, without limitation. In some embodiments, method 600 may further include a step of retraining, by the at least a processor, the treatment machine-learning model as a function of the post-recommended treatment electrocardiogram and the recommended treatment outcome data. This may be implemented as disclosed with reference to FIGS. 1-5, without limitation. In some embodiments, the treatment recommendation may include a secondary ablation target. This may be implemented as disclosed with reference to FIGS. 1-5, without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
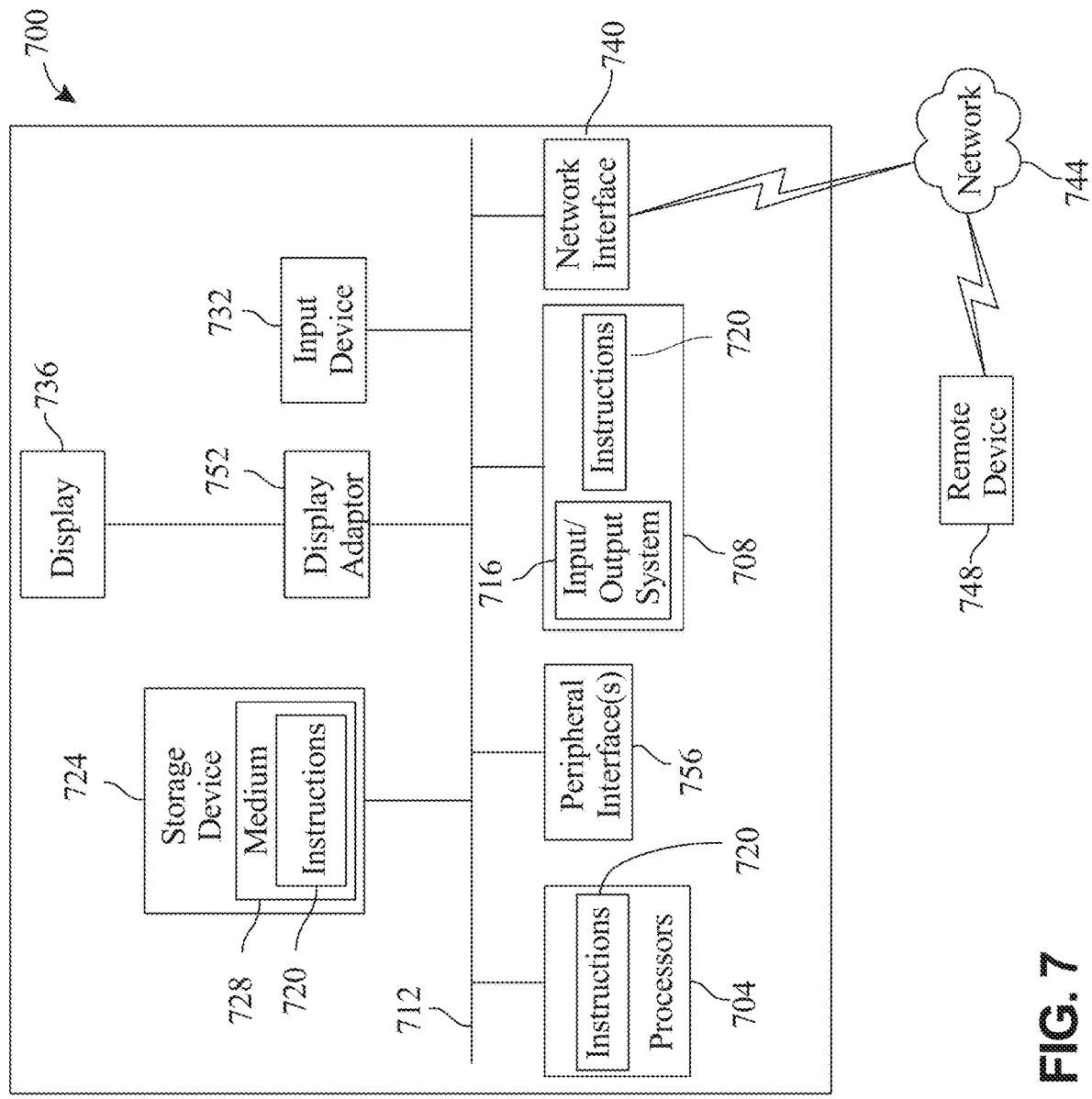
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display 736. Examples of a display device include, but are not limited to, a liquid crystal display (LCD), a cathode ray tube (CRT), a plasma display, a light emitting diode (LED) display, and any combinations thereof. Display adapter 752 and display 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for prediction of repeat ablation efficacy, the apparatus comprising:
   an electrocardiogram device, wherein the electrocardiogram device is configured to detect post-ablation arrhythmic electrocardiogram (ECG) data representative of a post-ablation arrhythmia of a patient who has previously undergone an ablation procedure at a primary ablation target;
   at least a processor; and
   a memory communicatively connected to the at least a processor, wherein the memory contains instructions configuring the at least a processor to:
      receive, from the electrocardiogram device, the post-ablation arrhythmic ECG data;
      generate, using a repeat-ablation efficacy machine-learning model, repeat-ablation efficacy data representing predicted efficacy of a repeat ablation procedure to resolve an arrhythmia of the patient, wherein generating the repeat-ablation efficacy data of the patient comprises:
         iteratively training the repeat-ablation efficacy machine-learning model using training data, wherein ablation evaluation machine-learning model is trained and retrained until it surpasses an accuracy threshold, wherein new patient data is periodically integrated into the training data;
         inputting, into the repeat-ablation efficacy machine-learning model, the post-ablation arrhythmic ECG data; and
         receiving as output, from the repeat-ablation efficacy machine-learning model, the repeat-ablation efficacy data;
      generate, using a treatment machine-learning model, a treatment recommendation based on the repeat-ablation efficacy data, the treatment recommendation comprising performing a repeat ablation procedure at a secondary ablation target on the patient; and
      transmit, for display, the repeat-ablation efficacy data; and
   an ablation device configured to perform the repeat ablation procedure at the secondary ablation target on the patient according to the generated treatment recommendation to increase a likelihood of success of the repeat ablation procedure.

2. The apparatus of claim 1, wherein the repeat-ablation efficacy data comprises a predicted chance of pulmonary vein reconnection.

3. The apparatus of claim 1, wherein generating the ablation training data from the subset of patient health records comprises de-identifying the subset of patient health records.

4. The apparatus of claim 1, wherein the repeat-ablation efficacy data comprises a quantitative value or a classification.

5. The apparatus of claim 1, wherein determining the treatment recommendation comprises generating, using the treatment machine-learning model, the treatment recommendation as a function of the post-ablation arrhythmic ECG electrocardiogram-data.

6. The apparatus of claim 5, wherein determining a treatment recommendation comprises:
   receiving treatment training data, wherein the treatment training data comprises historical ECG data correlated to historical treatment data;
   training the treatment machine-learning model using the treatment training data; and
   generating the treatment recommendation using the trained treatment machine-learning model.

7. The apparatus of claim 5, wherein:
   the apparatus further comprises a display device; and
   the memory contains instructions further configuring the at least a processor to display the treatment recommendation using the display device.

8. The apparatus of claim 5, wherein the memory contains instructions further configuring the at least a processor to:
   receive a post-recommended treatment ECG and recommended treatment outcome data; and
   retrain the treatment machine-learning model as a function of the post-recommended treatment ECG and the recommended treatment outcome data.

9. The apparatus of claim 1, wherein:
   the memory further comprises instructions configuring the at least a processor to receive prior-procedure intracardiac echocardiogram data; and
   generating the repeat-ablation efficacy data of the patient further comprises inputting, into the repeat-ablation efficacy machine-learning model, the prior-procedure intracardiac echocardiogram data.

10. The apparatus of claim 1, wherein:
    the memory further comprises instructions configuring the at least a processor to receive prior-procedure ablation parameter data; and
    generating the repeat-ablation efficacy data of the patient further comprises inputting, into the repeat-ablation efficacy machine-learning model, the prior-procedure ablation parameter data.

11. A method for prediction of repeat ablation efficacy, the method comprising:
    detecting, using an electrocardiogram device, post-ablation arrhythmic electrocardiogram (ECG) data representative of a post-ablation arrhythmia of a patient who has previously undergone an ablation procedure at a primary ablation target;
    receiving, by at least a processor, from the electrocardiogram device, the post-ablation arrhythmia ECG data;
    generating, by the at least a processor and using a repeat-ablation efficacy machine-learning model, repeat-ablation efficacy data representing predicted efficacy of a repeat ablation procedure to resolve an arrhythmia of the patient, wherein generating the repeat-ablation efficacy data of the patient comprises:
       iteratively training the repeat-ablation efficacy machine-learning model using the training data, wherein ablation evaluation machine-learning model is trained and retrained until it surpasses an accuracy threshold, wherein new patient data is periodically integrated into the training data;
       inputting, into the repeat-ablation efficacy machine-learning model, the post-ablation arrhythmic ECG data; and receiving as output, from the repeat-ablation efficacy machine-learning model, the repeat-ablation efficacy data;

transmitting, by the at least a processor, for display, the repeat-ablation efficacy data;

generating, using a treatment machine-learning model, a treatment recommendation based on the repeat-ablation efficacy data, the treatment recommendation comprising performing a repeat ablation procedure at a secondary ablation target on the patient; and performing the repeat ablation procedure at the secondary ablation target on the patient according to the generated treatment recommendation to increase a likelihood of success of the repeat ablation procedure.

12. The method of claim 11, wherein the repeat-ablation efficacy data comprises a predicted chance of pulmonary vein reconnection.

13. The method of claim 11, wherein generating the ablation training data from the subset of patient health records comprises de-identifying the subset of patient health records.

14. The method of claim 11, wherein the repeat-ablation efficacy data comprises a quantitative value or a classification.

15. The method of claim 11, wherein determining the treatment recommendation comprises generating, using the treatment machine-learning model, the treatment recommendation as a function of the post-ablation arrhythmic ECG data.

16. The method of claim 15, wherein determining a treatment recommendation comprises:

receiving treatment training data, wherein the treatment training data comprises historical ECG data correlated to historical treatment data;

training the treatment machine-learning model using the treatment training data; and generating the treatment recommendation using the trained treatment machine-learning model.

17. The method of claim 15 further comprising displaying, using a display device, the treatment recommendation.

18. The method of claim 15, further comprising:

receiving, by the at least a processor, a post-recommended treatment ECG and recommended treatment outcome data; and retraining, by the at least a processor, the treatment machine-learning model as a function of the post-recommended treatment ECG and the recommended treatment outcome data.

19. The method of claim 1, wherein:

the method further comprises receiving, by the at least a processor, prior-procedure intracardiac echocardiogram data; and generating the repeat-ablation efficacy data of the patient further comprises inputting, into the repeat-ablation efficacy machine-learning model, the prior-procedure intracardiac echocardiogram data.

20. The method of claim 11, wherein:

the method further comprises receiving, by the at least a processor, prior-procedure ablation parameter data; and generating the repeat-ablation efficacy data of the patient further comprises inputting, into the repeat-ablation efficacy machine-learning model, the prior-procedure ablation parameter data.

* * * * *